United States Patent
Lewis et al.

(10) Patent No.: US 7,273,949 B2
(45) Date of Patent: Sep. 25, 2007

(54) SALTS AND METHODS FOR THEIR PREPARATION

(75) Inventors: Samuel J. Lewis, Duncan, OK (US); Michael J. Szymanski, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 147 days.

(21) Appl. No.: 11/198,027

(22) Filed: Aug. 5, 2005

(65) Prior Publication Data

US 2007/0032550 A1 Feb. 8, 2007

(51) Int. Cl.
*C07C 309/00* (2006.01)
*C04B 7/00* (2006.01)
*C04B 16/00* (2006.01)

(52) U.S. Cl. ............. 562/102; 562/109; 106/638; 106/802; 106/810

(58) Field of Classification Search ............ 562/102, 562/109
See application file for complete search history.

(56) References Cited

U.S. PATENT DOCUMENTS

| | | | | |
|---|---|---|---|---|
| 3,359,225 | A | * | 12/1967 | Welsend |
| 4,522,653 | A | * | 6/1985 | Rao et al. |
| 4,557,763 | A | * | 12/1985 | George et al. |
| 4,640,942 | A | | 2/1987 | Brothers .......... 523/130 |
| 4,818,288 | A | * | 4/1989 | Aignesberger et al. |
| 4,987,249 | A | * | 1/1991 | Sandler |
| 5,025,104 | A | | 6/1991 | Sandler |
| 5,041,630 | A | | 8/1991 | Patel et al. .......... 562/41 |
| 5,287,929 | A | * | 2/1994 | Bloys et al. |
| 6,019,835 | A | * | 2/2000 | Chatterji et al. |
| 6,182,758 | B1 | * | 2/2001 | Vijn |
| 6,591,910 | B1 | * | 7/2003 | Chatterji et al. |
| 6,739,806 | B1 | * | 5/2004 | Szymanski et al. |
| 6,843,846 | B2 | * | 1/2005 | Chatterji et al. |
| 2004/0144537 | A1 | * | 7/2004 | Reddy et al. |
| 2005/0092211 | A1 | * | 5/2005 | Lewis et al. |

OTHER PUBLICATIONS

Product Brochure for CFR-2 cement friction reducer, Halliburton Energy Services, (1999).*
Product Brochure for CFR-3 cement friction reducer, Halliburton Energy Services, (2004).*
Product Brochure for CFR-4 cement friction reducer, Halliburton Energy Services, (1999).*
Product Brochure for CFR-6 cement friction reducer, Halliburton Energy Services, (1999).*
Lewis, S.J. et al., "Methods for Sealing In Subterranean Zones Using Salts" filed Aug. 5, 2005 as U.S. Appl. No. 11/198,026.
Lewis, S.J. et al., "Cementing Compositions Including Salts" filed Aug. 5, 2005 as U.S. Appl. No. 11/198,028.
Foreign communication from a related counter-part application dated Nov. 6, 2006.
Office action dated Sep. 21, 2006 from U.S. Appl. No. 11/198,028.
Office action dated Feb. 2, 2007 from U.S. Appl. No. 11/198,026.
Notice of Allowability from U.S. Appl. No. 11/198,028 dated May 18, 2007.
Office Action from U.S. Appl. No. 11/198.026 dated Jun. 5, 2007.

* cited by examiner

*Primary Examiner*—Sikarl A. Witherspoon
(74) *Attorney, Agent, or Firm*—Craig W. Roddy; Haynes & Boone

(57) ABSTRACT

Disulfonate salts of 2,4-pentanedione and methods for making such salts are described. The disulfonate salts are useful as cement dispersants. Cement compositions including such salts, methods for making cement compositions including such salts, and methods for performing cementing operations using such cement compositions are also described.

19 Claims, No Drawings

SALTS AND METHODS FOR THEIR PREPARATION

BACKGROUND

The present disclosure relates generally to salts that are useful as cement dispersants, methods for making such salts, cement compositions incorporating such salts, and methods for cementing using cement compositions incorporating such salts. In particular, a disulfonate salt of 2,4-pentanedione and methods for making and using such a salt are described.

Cement dispersants are often used in cement compositions utilized in construction for facilitating the mixing of the cement compositions. Also, in the cementing of oil and gas wells and the like, dispersants are extensively used to reduce the apparent viscosities of the cement compositions utilized. The reduction of the apparent viscosity of a cement composition allows the cement composition to be pumped with less friction pressure and less pump horsepower. In addition, the lower apparent viscosity often allows the cement composition to be pumped in turbulent flow. Turbulent flow characteristics are desirable when pumping cement compositions in oil and gas wells to more efficiently remove drilling fluid from surfaces in the well bore as the drilling fluid is displaced by the cement composition being pumped. The inclusion of dispersants in cement compositions is also desirable in that the presence of the dispersants reduces the water required for preparation of the cement compositions. Cement compositions having a reduced water content are characterized by improved compressive strength development.

A number of dispersing agents have been utilized heretofore in cement compositions, particularly in cement compositions used for primary and remedial cementing in oil and gas wells. For example, certain organic acids, such as gluconic acid and citric acid, have been used as cement dispersants. However, such organic acids are also strong set retarding agents. That is, the presence of an organic acid dispersant in a cement composition prevents the cement composition from setting for a relatively long period of time. Such a delayed set is often costly or otherwise detrimental. Other dispersants that are commonly used in hydraulic cement compositions include polynapthalene sulfonate, poly-B-naphthol sulfonate, polymelamine sulfonate, and many others. While such dispersants function very well in cement compositions, they can be environmentally unacceptable, especially in offshore operations where particular ecological properties may be required.

DESCRIPTION

According to embodiments described herein, a method of cementing is provided. The method includes introducing a cement composition comprising cementitious material, mixing fluid and a disulfonate salt of 2,4-pentanedione into an area to be cemented, and allowing the cement composition to set therein. In certain embodiments, the 2,4-pentanedione disulfonate salt acts as a cement dispersant. According to certain embodiments, the area to be cemented is in a subterranean zone, which may be penetrated by a well bore.

According to other embodiments described herein, methods of preparing a disulfonate salt of 2,4-pentanedione are provided. According to one such method, 2,4-pentanedione is sulfonated by reacting it with a sulfur source, for example, chlorosulfonic acid. The molar ratio of the sulfur source to 2,4-pentanedione is in the range of from about 4:1 to about 1:1 in some embodiments, in the range of from about 3:1 to about 2:1 in other embodiments, or in the range of from about 3.5:1 to about 2.5:1 in still other embodiments. The resulting product includes 2,4-pentanedione-1,5-disulfonic acid, and other acid by-products, such as hydrochloric and sulfuric acids, and/or mono-sulfonic acids.

The resulting product is then reacted with a base, for example, sodium hydroxide, to neutralize the 2,4-pentanedione-1,5-disulfonic acid, thereby forming a salt of 2,4-pentanedione. The amount of base reacted with the resulting product is that amount that will neutralize at least a portion of the 2,4-pentanedione-1,5-disulfonic acid. In certain embodiments, the base is added until the resulting product is neutralized to a pH of about 7. Any other acids, such as hydrochloric, sulfuric, or mono-sulfonic acids that may be present as by-products, may also be neutralized by reaction with the base.

The neutralized product is then rinsed with a rinsing agent, for example, methanol, to remove other acid by-products, such as hydrochloric and sulfuric acids, and/or mono-sulfonic acids, and/or to remove other salts formed by the neutralization, such as salts of hydrochloric and sulfuric acids, and/or mono-sulfonic acids. It was discovered that hydrophobic solvents, such as methanol, would remove the by-product acids and/or salts, while leaving the salt of 2,4-pentanedione-1,5 disulfonic acid primarily undissolved.

According to other examples, the rinsing agent can be another hydrophobic solvent such as ethanol, or can be a polar solvent such as dimethylformamide ("DMF"), or can be any other solvent that will remove or dissolve the by-products, and not the disulfonate salt.

According to some exemplary methods for preparing a disulfonate salt of 2,4-pentanedione, the reaction of 2,4-pentanedione with a sulfur source is conducted in an inert solvent. The reaction solvent can be chloroform, or a halogenated hydrocarbon such as carbon tetrachloride, 1,1,1-trichloroethane, 1,1,2-trichloroethane, 1,1,1,2-tetrachloroethane and 1,1,2,2-tetrachloroethane.

According to other embodiments for preparing a disulfonate salt of 2,4-pentanedione, the reaction of 2,4-pentanedione with a sulfur source is conducted without a solvent. In still other examples, the reaction occurs in an inert atmosphere. According to one such example, the inert atmosphere comprises nitrogen.

According to some exemplary methods for preparing a disulfonate salt of 2,4-pentanedione, the base that is reacted with the reaction product of 2,4-pentanedione and a sulfur source comprises an alkali metal or an alkaline earth metal. According to one example of such methods, the base is sodium hydroxide, and the neutralization reaction results in the formation of 2,4-pentanedione-1,5-sodium disulfonate, and may also result in other salts from acid by-products that may have been present. According to other embodiments, a potassium salt, a magnesium salt, a barium salt, an ammonium salt, a calcium salt or a cesium salt of 2,4-pentanedione is prepared by reacting the reaction product of 2,4-pentanedione and a sulfur source with a base derived from potassium, magnesium, barium, ammonium, calcium or cesium. Suitable sources include but are not limited to hydroxides of potassium, magnesium, barium, ammonium, calcium and cesium. The resulting salts would include 2,4-pentanedione-1,5-potassium disulfonate; 2,4-pentanedione-1,5-magnesium disulfonate; 2,4-pentanedione-1,5-barium disulfonate; 2,4-pentanedione-1,5-ammonium disulfonate; 2,4-pentanedione-1,5-calcium disulfonate; and 2,4-pentanedione-1,5-cesium disulfonate, respectively.

According to still other embodiments, sulfonation of 2,4-pentanedione is achieved using oleum (fuming sulfuric acid) which is commercially available from numerous sources including DuPont. In still other alternative embodiments, sulfonation of 2,4-pentanedione is achieved using a falling film sulfur trioxide sulfonation, equipment for which is commercially available from sources such as Chemithon Corporation. In still other embodiments, a 2,4-pentanedione-1,5-disulfonic acid is prepared as described in U.S. Pat. No. 4,987,249 to Sandier, the entire disclosure of which is hereby incorporated herein by reference, and is converted to the salt by reaction with a base comprising an alkali metal or an alkaline earth metal as described above. Exemplary bases include but are not limited to sodium hydroxide, potassium hydroxide, magnesium hydroxide, barium hydroxide, ammonium hydroxide, calcium hydroxide and cesium hydroxide.

According to still other embodiments described herein, a disulfonate salt of 2,4-pentanedione is provided. According to one such embodiment, the salt comprises 2,4-pentanedione-1,5-sodium disulfonate. According to another such embodiment, a disulfonate salt of 2,4-pentanedione has an environmentally acceptable toxicity. As used herein, the term "environmentally acceptable toxicity" means that, when tested according to procedures that are the same as or equivalent to those set forth by the OSPAR Guidelines for Completing the Harmonised Offshore Chemical Notification Format (HOCNF) (References number: 2003-1) that were in effect on Dec. 31, 2004, the salt is determined to have a toxicity of greater than about 10,000 mg/L for an algae (*skeletonema costatum*), a crustacean (*acartia tonsa*), a fish (*scopthalmus*) and a sediment reworker (*corophium volutator*).

OSPAR is a commission for protection of the marine environment in the North-East Atlantic Sea. The HOCNF protocols in effect on Dec. 31, 2004 are known to those of ordinary skill in the art, and therefore need not be detailed herein. Generally, however, the toxicity tests are conducted with a known number of organisms (e.g., an algae, a crustacean, a fish, and a sediment reworker) in a known amount of water. The test substance, which may be any of the disulfonate salts of 2,4-pentanedione described herein, is added to the water until the organisms die or become incapacitated. The amount of 2,4-pentanedione disulfonate salt required to kill or incapacitate half the test population is divided by the amount of water to give mg/L.

According to yet another embodiment, a disulfonate salt of 2,4-pentanedione has a "nationally acceptable toxicity." As used herein, the term "nationally acceptable toxicity" means that when tested according to procedures that are the same as or equivalent to those in effect in a country of interest on Dec. 31, 2004, the salt is determined to have a toxicity acceptable for use in the areas subject to such country's procedures.

According to one such embodiment, a disulfonate salt of 2,4-pentanedione has a nationally acceptable toxicity for the United Kingdom. According to this embodiment, the salt would qualify for a gold ranking under the chemical ranking scheme employed in the United Kingdom on Dec. 31, 2004. This chemical ranking scheme uses data established under the prescreening criteria set by the Harmonised Mandatory Control System established by OSPAR and the CHARM (Chemical Hazard Assessment and Risk Management) algorithm to assign a hazard quotient to a chemical, which quotient then correlates with a color on the following color scale (from most acceptable to least acceptable): gold, silver, white, blue, orange and purple.

According to another such embodiment, a disulfonate salt of 2,4-pentanedione has a nationally acceptable toxicity for Norway. According to this embodiment, the salt would qualify for a yellow ranking under the chemical ranking scheme employed in Norway on Dec. 31, 2004. Under the Norway ranking scheme, a black ranking indicates that the subject ingredient cannot be used in operations in the Norwegian sector of the North Sea, a red ranking indicates that the subject ingredient can only be used for a certain period of time in the Norwegian sector of the North Sea, and a yellow ranking indicates that the subject ingredient is acceptable for most operations in the Norwegian sector of the North Sea. The Norway ranking scheme also uses data established under the Harmonised Mandatory Control System, for example the BODIS (Biological Oxygen Demand of Insoluble Substance) and log $P_{ow}$ (log of the octanol-water partition coefficient) values of the subject ingredient. OSPAR, the Harmonised Mandatory Control System, the CHARM algorithm, and the ranking schemes of OSPAR member countries such as the United Kingdom and Norway, and techniques for evaluating a chemical according to such systems and schemes, are known to those of ordinary skill in the art.

A 2,4-pentanedione disulfonate salt as described herein has a variety of uses, one of which is as an ingredient in cement compositions. Thus, cement compositions comprising cementitious material, mixing fluid and a disulfonate salt of 2,4-pentanedione are described herein. Such cement compositions can include any of a variety of cementitious materials, including but not limited to hydraulic cements. Hydraulic cements set and harden by reaction with water, and include Portland cements, pozzolan cements, gypsum cements, aluminous cements, silica cements, and alkaline cements. According to certain of the present embodiments, the cementitious material comprises at least one API Portland cement. As used herein, the term "API Portland cement" means any cement of the type defined and described in API Specification 10, 5th Edition, Jul. 1, 1990, of the American Petroleum Institute, which includes Classes A, B, C, G, and H. According to certain examples disclosed herein, the cementitious material comprises any of Classes G and H cement. The preferred amount of cementitious material is understandably dependent on the cementing operation.

According to certain embodiments, the 2,4-pentanedione disulfonate salt included in a cement composition is selected from the group consisting of 2,4-pentanedione-1,5-sodium disulfonate; 2,4-pentanedione-1,5-potassium disulfonate; 2,4-pentanedione-1,5-magnesium disulfonate; 2,4-pentanedione-1,5-barium disulfonate; 2,4-pentanedione-1,5-ammonium disulfonate; 2,4-pentanedione-1,5-calcium disulfonate; and 2,4-pentanedione-1,5-cesium disulfonate.

The 2,4-pentanedione disulfonate salt can be mixed with the cementitious material as a dry ingredient, or can be mixed with the cementitious material as a solution. The amount of 2,4-pentanedione disulfonate salt to include in a cement composition depends upon the application to be made with the cement composition. However, according to one embodiment, a disulfonate salt of 2,4-pentanedione is present in a cement composition in an amount effective to reduce the apparent viscosity of the cement composition. Thus, a disulfonate salt of 2,4-pentanedione as described herein is suitable for use as a dispersant. According to other embodiments, a disulfonate salt of 2,4-pentanedione is present in a cement composition in an amount of from about 0.01% to about 5% by weight of the cementitious material. According to still other embodiments, a disulfonate salt of 2,4-pentanedione is present in a cement composition in an amount of from about 0.1% to about 4% or from about 0.1% to about 3% by weight of the cementitious material in the composition.

According to certain examples of cement compositions illustrated herein, the mixing fluid comprises water. Preferably, the water is present in an amount sufficient to make a slurry of a desired density from a mix comprising cementitious material and a disulfonate salt of 2,4-pentanedione. The water used to form a slurry can be fresh water, unsaturated salt solution, including brines and seawater, and saturated salt solution. Generally, any type of water can be used, provided that it does not contain an excess of compounds known to those of ordinary skill in the art to adversely affect properties of the cement composition. According to one embodiment, the water is present in an amount of about 20% to about 200% by weight of the cementitious material. According to other embodiments, water is present in an amount of from about 25% to about 150%, about 30% to about 100%, or about 30% to about 70% by weight of the cementitious material.

According to still other exemplary cement compositions, any of a variety of additives known to those of ordinary skill in the art may be included. Such additives may include density modifying materials (e.g., silica flour, sodium silicate, microfine sand, iron oxides and manganese oxides), dispersing agents, retarding agents, accelerating agents, fluid loss control agents, strength retrogression control agents, defoaming agents, gas migration agents, flow enhancing agents, surfactants, and viscosifying agents.

The following examples are illustrative of the foregoing methods and compositions.

EXAMPLE 1

A disulfonate salt of 2,4-pentanedione was prepared by first adding 575.7 ml (1009.2 g, 8.66 mol) of chlorosulfonic acid to about 1 L of chloroform in a 3 L round bottom flask equipped with a nitrogen adapter to maintain an inert atmosphere, a water condenser (to minimize chloroform evaporation), and another nitrogen adapter to vent liberated gases.

The resulting solution was cooled to 0° C., and 403.8 ml (393.7 g, 3.93 mol) of 2,4-pentanedione was slowly added via a pressure-equalized slow addition funnel. The solution was stirred and maintained at 0° C. throughout the addition process. After completing the addition of the 2,4-pentanedione, the temperature of the solution was raised to 60° C., and the solution was stirred overnight.

During the temperature increase, hydrochloric acid was liberated and was vented into a fume hood. After the hydrochloric acid evolution ceased, the reaction mixture was stirred while slowly cooling to room temperature. The resulting dark red viscous liquid was quenched with about 1 L of water and separated from the chloroform via a separatory funnel to result in an acid product that included 2,4-pentanedione-1,5-disulfonic acid, hydrochloric and sulfuric acids. The acid product was then neutralized to a pH of about 7, which resulted in the formation of 2,4-pentanedione-1,5-sodium disulfonate. The neutralization was performed by slowly adding 314.4 grams (about 2 molar equivalents of the 2,4-pentanedione-1,5-disulfonic acid ) of sodium hydroxide under atmospheric conditions. The reaction is extremely exothermic, therefore the sodium hydroxide was added slowly so that atmospheric conditions could be maintained. The hydrochloric and sulfuric acid by-products can be neutralized into NaCl (from the hydrochloric acid) and $Na_2SO_4$ (from the sulfuric acid) with additional sodium hydroxide.

The neutralized product was then rinsed several times with methanol to remove by-product acids, or any salts formed therefrom, while leaving the 2,4-pentanedione-1,5-sodium disulfonate primarily undissolved. When compared to the 2,4-pentanedione-1,5-disulfonic free acid, the 2,4-pentanedione-1,5-disulfonic salt was significantly less soluble, which was unexpected because with many substances, like aromatic salts, the salt is more soluble than the free acid. The rinsed product was dried in a vacuum oven and filtered through a 300 mesh screen to afford a flowing pale orange/red powder. The resulting powder was 2,4-pentanedione-1,5-sodium disulfonate.

The particular amounts recited in this Example 1 are illustrative only, as amounts other than those recited above can be used to render molar ratios of reaction and/or neutralization ingredients suitable for preparing a disulfonate salt of 2,4-pentanedione as disclosed herein.

EXAMPLE 2

Example 2 illustrates an exemplary use for a 2,4-pentanedione disulfonate salt. While the salt has other utilities, this Example 2 illustrates use of the salt as a dispersant in cement compositions.

Sixteen cement compositions (Composition Nos. 1-16) and certain properties of such compositions are described in Table 1. Each of the compositions was prepared from a base of 100% cementitious material. The cementitious material for Composition Nos. 1-12 and 15-16 was API Class G cement obtained from Dyckerhoff AG. The cementitious material for Composition No. 13 was API Class H cement obtained from LaFarge Corp.'s Joppa plant in Illinois. The cementitious material for Composition No. 14 was API Class H cement obtained from Texas Industries, Inc. ("TXI").

A dispersant and other additives (where indicated) were added to the base of each cement composition (i.e., to the cementitious material) in the amounts reported in Table 1, where "% bwoc" indicates a weight percentage by total weight of the cementitious material.

Dispersant Type A used for Composition Nos. 1, 5, 7, 10, 11 and 13-16 comprised a disulfonate salt of 2,4-pentanedione as a dispersant. The 2,4-pentanedione disulfonate salt used for the compositions of Example 2 was 2,4-pentanedione-1,5 sodium disulfonate prepared according to Example 1, however, a 2,4-pentanedione disulfonate salt can be obtained by other methods as discussed herein.

Dispersant Type B used for Composition Nos. 2, 6 and 8 comprised a condensation product of formaldehyde, acetone and a sulfite, which is a known dispersant commercially available under the tradename CFR-3™ from Halliburton Energy Services, Duncan, Okla.

Dispersant Type C used for Composition Nos. 3 and 9 comprised a phenolic hydroxyl group blocked alkali metal lignosulfonate, which is a known dispersant commercially available under the tradename CFR-5™ from Halliburton Energy Services, Duncan, Okla.

Composition Nos. 4 and 12 did not include a dispersant.

Other Additive Type D, used for Composition Nos. 1-3, comprised a grafted lignin as a retarder, which is commercially available under the tradename FDP601™ from Halliburton Energy Services, Duncan, Okla.

Other Additive Type E indicates a group of additives, each available from Halliburton Energy Services, Duncan, Okla., that were used to form Composition Nos. 7-9. The additives indicated by Type E according to the embodiments illustrated by Composition Nos. 7-9 comprised: 0.5% bwoc of a gas migration agent comprising silica, which is available under the tradename Gascon™; 1.1% bwoc of a retarder comprising a refined lignosulfate, which is available under the tradename HR-5L™; 0.2% bwoc of a defoaming agent comprising a seed oil and surfactants, which is available under the tradename NF-6™; 0.1% bwoc of a flow enhancing agent comprising a silica supported acid, which is commercially available under the tradename EZFlo™; 5.5% bwoc of a fluid loss agent comprising a cellulose, which is commercially available under the tradename Halad 613™; and 2.2% bwoc of a fluid loss agent comprising a grafted acrylic polymer, which is commercially available under the tradename Halad 600™. Each additive in the group of additives indicated by the designation "E" was mixed with the cement, dispersant, and mixing fluid to form Composition Nos. 10-12.

Other Additive Type F, used for Composition Nos. 10-11, comprised a refined lignosulfonate, which is commercially available as a retarder under the tradename HR-5 from Halliburton Energy Services, Duncan, Okla.

blend") and then added over a 15 second period to mixing fluid being maintained in a blender at 4000 RPM. When all of the dry blend was added to the mixing fluid, a cover was placed on the blender and mixing was continued at about 12,000 RPM for about 35 seconds. For each cement composition, the mixing fluid comprised water in the amount as listed in Table 1, where "% bwoc" indicates a weight percentage by total weight of the cementitious material. The density (lb/gal) of each composition is reported in Table 1.

The plastic viscosity ("PV"), yield point ("YP") and thickening time ("TT") were also tested for the compositions indicated in Table 1, at the test temperatures indicated in Table 1. Each of the plastic viscosity, yield point and thickening time was tested (where indicated) according to procedures well known to those of ordinary skill in the art, and which are described in API Specification RP 10B, 22nd Edition, 1997, of the American Petroleum Institute. In Table 1, the results of the PV tests are reported in centipoises and the results of the YP tests are reported in Pascals. The results of the TT tests are reported in time (hours:minutes) that it took the composition to attain 100 Bearden units of consistency (BC) in a high pressure consistometer, determined as described in API Specification RP 10B referenced above.

TABLE 1

| No. | Mixing Fluid (% bwoc) | Dispersant Type and Amount (% bwoc) | Other Additive Type and Amount (% bwoc) | Density (lb/gal) | Test Temp (° F.) | PV (cp) | YP (Pascal) | TT Hrs:Mins |
|---|---|---|---|---|---|---|---|---|
| 1 | 35 | A 0.2 | D 0.1 | 16.92 | 80 | 96 | 8.2 | not tested |
| 2 | 35 | B 0.2 | D 0.1 | 16.92 | 80 | 89 | 1 | not tested |
| 3 | 35 | C 0.2 | D 0.1 | 16.92 | 80 | 127.4 | 7.4 | not tested |
| 4 | 41.80 | none | none | 16.14 | 80 | 55 | 11 | 3:28 |
| 5 | 41.80 | A 0.684 | none | 16.10 | 80 | 31 | 6 | 5:19 |
| 6 | 41.80 | B 0.684 | none | 16.10 | 80 | settle | settle | 8:38 |
| 7 | 41.80 | A 0.684 | E | 14.99 | 122 | 35.6 | 2 | 5:15 |
| 8 | 41.80 | B 0.684 | E | 14.99 | 122 | 45.4 | 0 | 7:30 |
| 9 | 41.80 | C 0.684 | E | 14.99 | 122 | 46.7 | 0 | 9:07 |
| 10 | 41.80 | A 0.684 | F 0.15 | 16.09 | 122 | 34.9 | 9.8 | 3:02 |
| 11 | 41.80 | A 0.684 | F 0.11 | 16.09 | 122 | 27.8 | 11.3 | 2:50 |
| 12 | 41.80 | none | none | 16.14 | 122 | not tested | not tested | 2:01 |
| 13 | 32 | A 0.45 | none | 17.31 | 80 | 44.8 | 5.9 | not tested |
| 14 | 29 | A 0.50 | none | 17.75 | 80 | 200 | 10 | not tested |
| 15 | 41.80 | A 0.684 | none | 16.10 | 122 | 65 | 16.9 | 2:38 |
| 16 | 41.80 | A 0.684 | none | 16.10 | 122 | 66.4 | 11.8 | 2:29 |

The procedure followed for preparing each cement composition with the cementitious materials, dispersant, additives and mixing fluid as described above was API Specification RP 10B, 22nd Edition, 1997, of the American Petroleum Institute, which is a specification known to those of ordinary skill in the art. Generally, according to said specification, the cementitious material, dispersant and other additive (where applicable) were dry-blended (the "dry Those of ordinary skill in the art understand that the presence of a dispersant in a cement composition affects the PV of the composition, as well as the YP. PV and YP indicate rheological properties of a cement composition, where PV is related to the mechanical friction between particles and YP is related to the force required to break interactive bonds between particles and then to produce movement. In any given application, it may be desirable to increase or decrease the PV or the YP of a cement composition to achieve rheological properties suitable for that application. Those of ordinary skill in the art understand that a desirable value for either PV or YP depends on the application (for example, the type of cementing being performed and the conditions under which the cementing will occur) being made with the cement composition. Generally, however, those of ordinary skill in the art understand that the thickness of a cement composition varies in direct relationship to the PV value of the cement composition. Cement compositions that are too thick for a given application have flowability problems. Thus, a desirable PV for a cement composition is one that, for a given application, is low enough to avoid flowability problems, but high enough to provide the cement composition with the desired rheological property for the given application. As to YP, those of ordinary skill in the art understand that, generally, the lower the YP of cement composition, the more likely it is that the constituents of the composition will settle out. Thus, a desirable YP is one that is high enough to prevent settling, but low enough to provide the cement composition with the desired rheological property for the given application.

Considering that a desirable value for either PV or YP depends on the application being made with the cement composition, the PV and YP data for Composition Nos. 1, 5, 7, 10, 11 and 13-16 illustrate that cement compositions that include a dispersant comprising a disulfonate salt of 2,4-pentanedione exhibit favorable rheological properties as compared to cement compositions comprising conventional dispersants (i.e., Composition Nos. 2, 3, 6, 8 and 9.)

In particular, a comparison between Composition Nos. 1-3, each of which comprised a different Dispersant Type, in equal amounts respectively, and the same Other Additive Type amount, in equal amounts, shows that Composition No. 1 (which comprised a disulfonate salt of 2,4-pentanedione and Additive Type D) has a PV value less than that of Composition No. 3 (which comprised CFR-5™ dispersant and Additive Type D), but a YP value greater than that of No. 3, thus making Composition No. 1 a more suitable cement composition for certain applications. As between Composition No. 2 (which comprised CFR-3™ dispersant and Additive Type D) and Composition No. 1, Composition No. 1 has a greater PV and larger YP value, thus making Composition No. 1 a more suitable cement composition for certain applications.

Composition No. 4, which included only water and cement, provides a control for comparison of compositions that included water, cement, and one of Dispersant Types A, B and C, such as Compositions Nos. 5 and 6. For example, a comparison between the PV, YP and TT values of Composition Nos. 4, 5 and 6 illustrates that cement compositions that include a disulfonate salt of 2,4-pentanedione (Dispersant Type A) have Theological properties and thickening times that make them more suitable for certain applications than cement compositions that do not include a disulfonate salt of 2,4-pentanedione (Composition No. 4), or that include a different Dispersant Type (Composition No. 6).

Further, Composition Nos. 5 and 6 are useful for comparing cement compositions that include, respectively, a disulfonate salt of 2,4-pentanedione as a dispersant (Dispersant Type A) and a conventional dispersing agent (Dispersant Type B), in equal amounts. The PV and YP data indicate that Composition No. 5 did not settle, while Composition No. 6 did. Those of ordinary skill in the art understand that settling is an undesirable occurrence for a cement composition. Thus, the PV and YP data indicate that a dispersant comprising a disulfonate salt of 2,4-pentanedione (Dispersant Type A) contributes favorable rheological properties to a cement composition. Moreover, the TT of Composition No. 5 was approximately 3 hours less than that of Composition No. 6. A shorter TT is desirable in certain cement applications, thus making a cement composition such as Composition No. 5 more suitable for certain applications.

Composition Nos. 7-9 illustrate compositions comprising the same type and amount of Other Additive (Type E), but equal amounts of different Dispersant Types. The PV and YP data indicate that Composition No. 8 (which comprised CFR-3™ dispersant and Additive Type E) exhibits PV and YP properties substantially similar to that of Composition No. 9 (which comprised CFR-5™ dispersant and Additive Type E). Composition No. 7, however, (which comprised a disulfonate salt of 2,4-pentanedione and Additive Type E) has a lower PV value, but a larger YP value, thus making Composition No. 7 more suitable than Composition Nos. 8 and 9 for certain applications. Moreover, the TT of Composition No. 7 was shorter than that of Composition Nos. 8 and 9, which makes a cement composition such as Composition No. 7 more suitable for applications where it is desirable to have a shorter TT.

Composition Nos. 10-11 illustrate compositions comprising equal amounts of Dispersant Type A (a disulfonate salt of 2,4-pentanedione), but different amounts of Other Additive Type F (a refined lignosulfonate retarder). Composition Nos. 10 and 11 illustrate that conventional retarders, such as Type F, are effective in cement compositions comprising a salt of 2,4-pentanedione. Such cement compositions achieve favorable Theological properties as indicated by the reported YP and PV values, and the retarder still functions to slow the TT's of such compositions.

Thus, the TT's of cement compositions that include a disulfonate salt of 2,4-pentanedione can be adjusted with conventional retarders. In any given application, it may be desirable to have a longer or shorter TT. The TT of Composition No. 12, which included only water and cement, provides a control for comparison of compositions that included Dispersant Type A, and optionally, retarding agents. For example, the TT of Composition Nos. 10 and 11 (each of which included a retarding agent) is longer than that of Composition No. 12. The TT of Composition Nos. 15 and 16 (each of which did not include a retarding agent) is also longer than that of Composition No. 12, although not as long as Composition Nos. 10 and 11.

Composition Nos. 13-16 illustrate compositions that include a disulfonate salt of 2,4-pentanedione as a dispersant in varying amounts. The PV and YP data for each of these compositions illustrate that the disulfonate 2,4-pentanedione salt is an effective dispersant in varying amounts over a broad temperature range. The amount of a disulfonate salt of 2,4-pentanedione to include in a cement composition as a dispersant according to the present embodiments depends upon the application to be made with the cement composition. However, according to one embodiment, a dispersant comprising a disulfonate salt of 2,4-pentanedione is present in a cement composition in an amount effective to reduce the apparent viscosity of the cement composition.

EXAMPLE 3

Example 3 illustrates an exemplary use for a 2,4-pentanedione disulfonate salt as an ingredient in cement compositions required to comprise ingredients meeting an environmentally acceptable toxicity or a nationally acceptable toxicity. A 2,4-pentadionedione disulfonate salt as described herein was determined to have an environmentally acceptable toxicity and a nationally acceptable toxicity. In particular, 2,4-pentanedione-1,5-sodium disulfonate prepared according to Example 1 was determined to have a toxicity of greater than about 10,000 mg/L for an algae (*skeletonema costatum*), a crustacean (*acartia tonsa*), a fish (*scopthalmus*) and a sediment reworker (*corophium volutator*).

In this Example 3, the toxicity results for the skeletonema costatum were determined according to ISO (International Organization for Standardization) 10253, the protocol for which is known to those of ordinary skill in the art, and is also the protocol required under the above-referenced HOCNF Guidelines. The toxicity results for the *acartia tonsa* were determined according to ISO 14669, the protocol for which is known to those of ordinary skill in the art. The toxicity results for the *scopthalmus* and the *corophium volutator* were determined according to Part B of the OSPAR Protocols on Methods for the Testing of Chemicals Used in the Offshore Industry (published by OSPAR in 1995).

A toxicity result of greater than about 10,000 mg/L for the species tested in this Example 3 indicates that 2,4-pentanedione-1,5-sodium disulfonate has a low toxicity such that it would have an environmentally acceptable toxicity and/or a nationally acceptable toxicity in at least one country of interest, for example the United Kingdom or Norway. Such toxicity acceptability makes 2,4-pentanedione-1,5-sodium disulfonate particularly useful for compositions required to meet a particular environmental standard. Other 2,4-pentanedione disulfonate salts as described herein should also have low toxicity such that they would have an environmentally acceptable toxicity and/or a nationally acceptable toxicity in at least one country of interest.

Other embodiments of the current invention will be apparent to those skilled in the art from a consideration of this specification or practice of the invention disclosed herein. However, the foregoing specification is considered merely exemplary of the current invention with the true scope and spirit of the invention being indicated by the following claims.

What is claimed is:

1. A disulfonate salt of 2,4-pentanedione.

2. The disulfonate salt of claim 1 wherein the salt is selected from the group consisting of 2,4-pentanedione-1,5-sodium disulfonate; 2,4-pentanedione-1,5-potassium disulfonate; 2,4-pentanedione-1,5-magnesium disulfonate; 2,4-pentanedione-1,5-barium disulfonate; 2,4-pentanedione-1,5-ammonium disulfonate; 2,4-pentanedione-1,5-calcium disulfonate; and 2,4-pentanedione-1,5-cesium disulfonate.

3. The disulfonate salt of claim 1 wherein the salt has an environmentally acceptable toxicity.

4. The disulfonate salt of claim 1 wherein the salt has a nationally acceptable toxicity.

5. The disulfonate salt of claim 1 wherein the salt qualifies for a gold ranking under the chemical ranking scheme employed in the United Kingdom on Dec. 31, 2004.

6. The salt of claim 1, wherein the salt qualifies for a yellow ranking under the chemical ranking scheme employed in Norway on Dec. 31, 2004.

7. The disulfonate salt of claim 1 wherein the salt has a toxicity of greater than about 10,000 mg/L for an algae, a crustacean, a fish and a sediment reworker.

8. A method for preparing a disulfonate salt of 2,4-pentanedione comprising: reacting 2,4-pentanedione with a sulfur source to form 2,4-pentanedione-1,5-disulfonic acid; reacting the 2,4-pentanedione-1,5-disulfonic acid with a base to form a disulfonate salt of 2,4-pentanedione; and rinsing the disulfonate salt of 2,4-pentanedione with a rinsing agent.

9. The method of claim 8 wherein the sulfur source comprises chiorosulfonic acid.

10. The method of claim 9 wherein the base comprises sodium hydroxide.

11. The method of claim 10 wherein the rinsing agent comprises methanol.

12. The method of claim 8 wherein the base is selected from the group consisting of sodium hydroxide, potassium hydroxide, magnesium hydroxide, barium hydroxide, ammonium hydroxide, calcium hydroxide and cesium hydroxide.

13. The method of claim 8 wherein the sulfur source comprises chiorosulfonic acid, fuming sulfuric acid, or falling film sulfur trioxide sulfonation.

14. The method of claim 8 wherein the sulfur source is chlorosulfonic acid, and the 2,4-pentanedione is reacted with the chlorosulfonic acid in a solvent.

15. The method of claim 14 wherein the solvent is selected from the group consisting of carbon tetrachloride, 1,1,1-trichloroethane, 1,1,2-trichloroethane, 1,1,1,2-tetrachloroethane and 1,1,2,2-tetrachloroethane.

16. The method of claim 8 wherein the molar ratio of the sulfur source to 2,4-pentanedione is in the range of from about 4:1 to about 1:1.

17. The method of claim 8 wherein reacting the base with the 2,4-pentanedione-1,5-disulfonic acid comprises adding the base to the 2,4-pentanedione-1,5-disulfonic acid to a pH of about 7.

18. The method of claim 8 wherein the base comprises a metal selected from the group consisting of alkali metals and alkaline earth metals.

19. The method of claim 8 wherein the rinsing agent is selected from the group consisting of methanol, ethanol and dimethylformamide.

* * * * *